US006392050B2

(12) United States Patent
Lui et al.

(10) Patent No.: US 6,392,050 B2
(45) Date of Patent: May 21, 2002

(54) PROCESS FOR PREPARING SUBSTITUTED PYRIDINES

(75) Inventors: Norbert Lui, Köln; Hans Panskus; Albert Schnatterer, both of Leverkusen, all of (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/873,740

(22) Filed: Jun. 4, 2001

(30) Foreign Application Priority Data

Jun. 8, 2000 (DE) .......................................... 100 28 414
Mar. 13, 2001 (DE) .......................................... 101 11 874

(51) Int. Cl.$^7$ .......................................... C07D 213/133
(52) U.S. Cl. ..................... 546/321; 546/286; 546/287; 546/318; 546/322; 546/326; 546/327; 546/330; 546/335; 546/341; 546/342; 546/346; 546/348
(58) Field of Search ................................. 546/286, 287, 546/318, 321, 322, 326, 327, 330, 335, 341, 342, 346, 348

(56) References Cited

U.S. PATENT DOCUMENTS 4,950,675 A 8/1990 Chucholowski ............. 514/336

OTHER PUBLICATIONS

J. Org. Chem. 62, (month unavailable) 1997, pp. 3582–3585, Takashi, Itoh, Kazuhiro Nagata, Yûji Matsuya, Michiko Miyazaki and Akio Ohsawa, Reaction of Nitric Oxide with Amines.

J. Med. Chem. 29, (month unavailable) 1986, pp. 1596–1603, Ronald H Böcker and F. Peter Guengereich, Oxidation of 4–Aryl–and 4–Alkyl–Substituted 2,6–Dimethyl–3,5–bis(alkoxycarbonyl)–1,4–dihydropyridines by Human Liver Microsomes and Immunochemical Evidence for the Involvement of Form of Cytochrome P–450.

Houben–Weyl: "Methoden der organischen Chemie, Bd. IV/1a", (month unavailable) 1981, Gerog Thieme Verlag, Stuttgart XP002174903, Seite 839–846, Tabelle 18, Seite 844 oberster Eintrag.

A. Hantzsch: "Ueberdie Synthese pyridinartiger Verbindungen aus Acetessigäther und Aldehydammoniak" Justus Liebigs Annalen Der Chemie, Bd. 215, (month unavailable) 1882, Seiten 1–81, XP001013491, Seite 21–22, Seite 42, Zeile 16–22.

*Primary Examiner*—Patricia L. Morris
(74) *Attorney, Agent, or Firm*—Joseph C. Gil; Richard E. L. Henderson

(57) ABSTRACT

The invention relates to a process for preparing substituted pyridines in a simple and cost-effective manner in good yields by reacting substituted 1,4-dihydropyridines with methyl nitrite in the presence of an acid that contains less than 20% by weight of oxidizing components.

10 Claims, No Drawings

PROCESS FOR PREPARING SUBSTITUTED PYRIDINES

BACKGROUND OF THE INVENTION

The present invention relates to an improved process for preparing substituted pyridines by oxidation (i.e., aromatization) of the corresponding 1,4-dihydropyridines.

Substituted pyridines are important products for the preparation of pharmaceutics, crop protection agents and dyes.

A large number of oxidizing agents, for example, supported iron nitrates and copper nitrates, if appropriate with the action of ultrasound, cerium ammonium nitrate, pyridinium chlorochromate, nitric acid, and nitrogen monoxide (see *J. Org. Chem.*, 62, 3582 (1997) are known to be suitable for oxidizing (i.e., aromatizing) 1,4-dihydropyridines. Some of these oxidation methods are expensive, others require complicated apparatus and safety precautions, and others require ecologically objectionable oxidizing agents. The nitrogen monoxide recommended in the above literature reference for use as oxidizing agent must be handled under argon since it reacts with atmospheric oxygen and is expensive. According to *J. Med. Chem.*, 29, 1596 (1986), the oxidation is carried out using nitric acid, but large amounts of nitric acid are required (12 ml of aqueous nitric acid for 0.66 g of starting material), and the product must be isolated by three extractions with ether.

To prepare 4-(4-fluorophenyl)-2,6-diisopropyl-3,5-di (methoxy-carbonyl) pyridine, it is known to oxidize the corresponding 1,4-dihydropyridine with sulfur (see U.S. Pat. No. 4,950,675). In addition to the problematic handling of sulfur, this process has the major disadvantage that yields of only considerably less than 40% are possible and that highly toxic hydrogen sulfide is formed as by-product.

Thus, there is currently no process that is easy to carry out and cost-effective and gives high yields for preparing substituted pyridines by oxidation of the corresponding 1,4-dihydropyridines.

SUMMARY OF THE INVENTION

This invention accordingly provides a process for preparing substituted pyridines of formula (I)

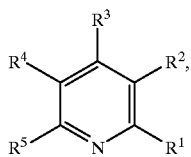

(I)

wherein
$R^1$ and $R^5$ are identical or different and each represents $C_1$–$C_{10}$-alkyl or $C_6$–$C_{10}$-aryl,
$R^2$ and $R^4$ are identical or different and each represents hydrogen, $C_1$–$C_{10}$-alkyl, CN, or $COOR^6$ wherein $R^6$ is $C_1$–$C_{10}$-alkyl, and
$R^3$ represents hydrogen, $C_1$–$C_{10}$-alkyl or represents $C_6$–$C_{10}$-aryl that is optionally substituted by halogen, nitro, $COOR^6$ (wherein $R^6$ is $C_1$–$C_{10}$-alkyl), CN, or $C_1$–$C_{10}$-alkyl,
comprising reacting a substituted 1,4-dihydropyridine of formula (II)

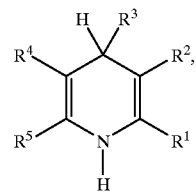

(II)

wherein $R^1$ to $R^5$ are as defined for formula (I),
with methyl nitrite in the presence of an acid containing less than 20% by weight of oxidizing components.

DETAILED DESCRIPTION OF THE INVENTION

In formulas (I) and (II), $R^1$ and $R^5$ are preferably identical and each preferably represents straight-chain or branched $C_1$–$C_6$-alkyl; $R^2$ and $R^4$ are preferably identical, and each preferably represents $COOR^6$ wherein $R^6$ is straight-chain or branched $C_1$–C6-alkyl; and $R^3$ preferably represents fluorine- and/or chlorine-substituted phenyl.

In formulas (I) and (II), $R^1$ and $R^5$ particularly preferably represent isopropyl; $R^2$ and $R^3$ particularly preferably represent $COOR^6$ wherein $R^6$ is methyl or ethyl; and $R^3$ particularly preferably represents 4-fluorophenyl.

The methyl nitrite that is required can be prepared in a simple known manner by reacting alkali metal nitrites with methanol in the presence of a strong acid. In this preparation method, the methyl nitrite is obtained in gaseous form and can be used in this form for the process according to the invention. It is advantageous to use at least the amount of methyl nitrite that is stoichiometrically required. Even relatively large excesses of methyl nitrite do not interfere with the reaction. Preference is given to using from I to 20 mol of methyl nitrite per mole of 1,4-dihydropyridine of formula (II).

A very wide variety of mineral and carboxylic acids are suitable for use as acids. Preference is given to using gaseous hydrogen chloride, aqueous hydrochloric acid, aqueous sulphuric acid and $C_1$–$C_4$-carboxylic acids in substance or as aqueous solution.

The amount of acid can be varied within relatively wide limits. It is possible, for example, to use catalytic, stoichiometric, or superstoichiometric amounts of acid. Preference is given to using from 0.01 to 2 mols of acid per mole of 1,4-dihydropyridine of formula (II). It is also possible to use mixtures of different acids. Carboxylic acids can also act as solvent and therefore can be set in higher molar ratios, for example up to 50 mols, preferably up to 30 mols per mol of 1,4-dihydropyridine of the formula (II).

The acid to be used contains less than 20% by weight of oxidizing components. Oxidizing components can be, for example, nitric acid or salts having oxidizing action. The content of oxidizing components in the acid is preferably below 5% by weight. Particularly preferably, the acid is free of oxidizing components.

The 1,4-dihydropyridine of formula (II) can also be employed in the form of 1,4-dihydropyridinium salts of non-oxidizing acids, for example, in the form of 1,4-dihydroxypyridine hydrochlorides. In such cases, it is possible to dispense with the separate addition of an acid.

If the acid is used in the form of an aqueous solution in such an amount that the reaction mixture forms a suspension or solution that is easy to stir, it is not necessary to add other solvents. Otherwise, it is expedient to add solvents. Suitable solvents are those that do not take part in any undesirable side reactions. Examples are water, aromatic hydro-carbons such as toluene, alcohols such as methanol, ethers such as dibutyl ether, halogenated hydrocarbons such as dichloroethane and chlorobenzene, sulfoxides such as dimethyl sulfoxide, and sulfones such as tetramethylene sulfone. Carboxylic acids can also act as solvent (see above).

If appropriate, the solvents are added in such amounts that the reaction mixture forms a suspension or solution that is easy to stir.

The process according to the invention can be carried out in different ways. For example, the 1,4-dihydropyridine of formula (II) can be suspended or dissolved in a solvent, followed by addition of the acid and introduction of gaseous methyl nitrite. It is also possible to admix the 1,4-dihydropyridine of formula (II) with such an amount of an aqueous solution of the acid that a readily stirrable suspension or solution is formed and then to introduce gaseous methyl nitrite. It is also possible to meter in the acid simultaneously but separately from the methyl nitrite.

Furthermore, it is also possible, for example, to suspend 1,4-dihydropyridine of formula (II) in water and then to introduce gaseous hydrogen chloride and then methyl nitrite. Other ways of carrying out the process according to the invention are also feasible.

Suitable reaction temperatures for the process according to the invention are, for example, between −30 and +100° C., in particular from −10 to +65° C.

The reaction mixture that is present after the reaction has ended can be worked up in a simple manner. If the reaction has been carried out substantially in aqueous medium, the reaction mixture can first be neutralized using any base, and the substituted pyridine of formula (I) that has been prepared can then be separated off, for example, by filtration.

If the reaction has been carried out substantially in alcoholic medium or in another water-miscible solvent, water can, after neutralization with any base, be added to the reaction mixture, and the substituted pyridine of formula (I) that has been prepared can be separated off, for example, by filtration.

If the reaction has been carried out in a water-immiscible medium, some or all of the solvent can, following neutralization with any base, be removed from the reaction mixture, thus giving the substituted pyridine of formula (I) that has been prepared.

Other simple alternatives for working up the reaction mixtures are also feasible.

The base used for neutralizing the reaction mixture can be any base that does not take part in undesirable side reactions. Suitable bases are, for example, aqueous lyes, alkoxides as such or in alcoholic solution, and amines. If the reaction is carried out in aqueous medium, preference is given to using aqueous lyes. If the reaction is carried out in an alcoholic medium, preference is given to alkoxides.

In cases where carboxylic acids are set in the neutralization can be omitted.

The process according to the invention has a number of advantages. Thus, the obtainable yields, which are generally between 90 and 99% of theory, are high, the practice is simple, the methyl nitrite can be prepared in a simple manner as required, no ecologically objectionable heavy metal salts are used for the oxidation and, as a consequence, no highly toxic by-products are formed, and work-up of the reaction mixture is simple.

EXAMPLES

Example 1 (not according to the invention)

The methyl nitrite used in the examples below was prepared as required by treating a solution of 1 part by weight of 25% by weight strength of aqueous sodium nitrite solution and 0.14 part by weight of methanol with 0.37 part by weight of 48% by weight strength aqueous sulfuric acid and used in gaseous form for the oxidation (i.e., aromatization) according to the invention of substituted 1,4-dihydropyridines of formula (II).

Example 2

In a 4 liter glass reactor, 750 g of 4-(4-fluorophenyl)-2,6-diisopropyl-3,5-di(methoxycarbonyl)-1,4-dihydropyridine were initially charged in 2250 g of water and 207 g of 37% by weight strength of aqueous hydrochloric acid. 15 mol of methyl nitrite were then introduced at 60° C. After cooling to 20° C., the pH was adjusted to pH 8 using 198 g of 45% by weight strength of aqueous sodium hydroxide solution. The resulting suspension was filtered and the product that had been filtered off was washed twice with in each case 800 ml of water and then dried at 55° C. under reduced pressure. 736 g of 4-(4-fluorophenyl)-2,6-diisopropyl-3,5-di(methoxycarbon) pyridine were isolated, which corresponds to a yield of 98% of theory.

Example 3

In a 2 liter glass reactor, 375 g of 4-(4-fluorophenyl)-2,6-diisopropyl-3,5-di (methoxycarbonyl)-1,4-dihydropyridine were dissolved in 711.6 g of methanol at −5° C. 4 g of gaseous hydrogen chloride and 2 mol of methyl nitrite were then introduced at from −3 to −10° C. After warming to 20° C., the mixture was neutralized by adding 19.5 g of 30% by weight strength of methanolic sodium methoxide solution. The solution was heated to boiling and then admixed with 170 g of water. After cooling to +5° C., the resulting suspension was filtered and the product that had been filtered off was washed twice with in each case 400 ml of methanol/water (1:4) and then dried at 55° C. under reduced pressure. This gave 338 g of 4-(4-fluoropheny)-2,6-diisopropyl-3,5-di(methoxycarbonyl)pyridine, which corresponds to a yield of 90.5% of theory.

Example 4

In a 4 1 glass reactor, 750 g 4-(4-fluorophenyl)-2,6-diisopropyl-3,5-di(methoxy-carbonyl)-1,4-dihydropyridine were mixed with 2250 g water and 245 g of acetic acid. Thereafter 7 mols of methyl nitrite were introduced at 58 to 60° C. After cooling to 20° C. 363 g of 45% by weight strength aqueous sodium hydroxide were added to result in an increase of the pH up to 9. The resulting suspension was filtered and the product that has been filtered off was washed twice with in each case 800 ml of water and then dried at 50 to 60° C. under reduced pressure. 708 g of 4-(4-fluoropheny)-2,6-diisopropyl-3,5-di(methoxy-carbonyl)-pyridine were isolated, which corresponds to a yield of 95% of theory.

Example 5

In a 4 1 glass reactor, 750 g 4-(4-fluorophenyl)-2,6-diisopropyl-3,5-di (methoxy-carbonyl)-1,4-dihydropyridine were mixed with 1470 g water and 1470 g of acetic acid. Thereafter 7 mols of methyl nitrite were introduced at 58 to 60° C. After cooling to 20° C. the resulting suspension was filtered and the product that has been filtered off was washed twice with in each case 800 ml of water and then dried at 50 to 60° C. under reduced pressure. 643 g of 4-(4-fluorophenyl)-2,6-diisopropyl-3,5-di(methoxy-carbon)-pryidine were isolated, which corresponds to a yield of 86% of theory.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a substituted pyridine of formula (I)

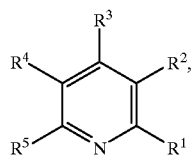

(I)

wherein $R^1$ and $R^5$ are identical or different and each represents $C_1$–$C_{10}$-alkyl or $C_6$–$C_{10}$-aryl, $R^2$ and $R^4$ are identical or different and each represents hydrogen, $C_1$–$C_{10}$-alkyl, CN, or $COOR^6$ wherein $R^6$ is $C_1$–$C_1$-alkyl, and $R^3$ represents hydrogen, $C_1$–$C_{10}$-alkyl or represents $C_6$–$C_{10}$-aryl that is optionally substituted by halogen, nitro, $COOR^6$ (wherein $R^6$ is $C_1$–$C_{10}$-alkyl), CN, or $C_1$–$C_{10}$-alkyl, comprising reacting a substituted 1,4-dihydropyridine of formula (II)

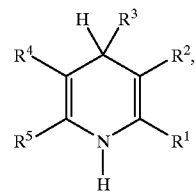

(II)

wherein $R^1$ to $R^5$ are as defined for formula (I), with methyl nitrite in the presence of an acid containing less than 20% by weight of oxidizing components.

2. A process according to claim 1 wherein in the formulas (I) and (II) $R^1$ and $R^5$ are identical and represent straight-chain or branched $C_1$–C6-alkyl; $R^2$ and $R^4$ are identical and represent $COOR^6$ wherein $R^6$ is straight-chain or branched $C_1$–$C_6$-alkyl; and $R^3$ represents fluorine- and/or chlorine-substituted phenyl.

3. A process according to claim 1 wherein the substituted 1,4-dihydropyridine starting material is 4-(4-fluorophenyl)-2,6-diisopropyl-3,5-di(methoxycarbonyl)-1,4-dihydropyridine and the substituted pyridine product is 4-(4-fluorophenyl)-2,6-diisopropyl-3,5-di (methoxycarbonyl)-pyridine.

4. A process according to claim 1 wherein the methyl nitrite is prepared by reacting an alkali metal nitrite with methanol in the presence of a strong acid and is used in an amount of from 1 to 20 mol of methyl nitrite per mole of 1,4-dihydropyridine of formula (II).

5. A process according to claim 1 wherein the acid is a mineral or carboxylic acid used in an amount of from 0.01 to 2 mols per mole of 1,4-dihydropyridine of formula (II).

6. A process according to claim 1 wherein the 1,4-dihydropyridine of formula (II) is employed in the form of a 1,4-dihydropyridinium salt of a non-oxidizing acid and the acid is not added separately.

7. A process according to claim 1 wherein the temperature is in the range from –30 to +100° C.

8. A process according to claim 1 wherein the acid is free of oxidizing components.

9. A process according to claims 1, wherein the gaseous hydrogen chloride, aqueous hydrochloric acid, aqueous sulfuric acid or a $C_1$–$C_4$-carboxylic acid in substance or as aqueous solution is used as acid.

10. A process according to claims 1, wherein a carboxylic acid is set in an amount of up to 50 mols per mol of 1,4-dihydropyridine of formula (II).

* * * * *